(12) United States Patent
Zuccolotto et al.

(10) Patent No.: US 8,214,012 B2
(45) Date of Patent: Jul. 3, 2012

(54) MAGNETIC RESONANCE IMAGING HAVING PATIENT VIDEO, MICROPHONE AND MOTION TRACKING

(75) Inventors: Anthony P. Zuccolotto, Freeport, PA (US); Walter Schneider, Pittsburgh, PA (US); Leroy K. Basler, Irwin, PA (US)

(73) Assignees: Psychology Software Tools, Inc., Pittsburgh, PA (US); University of Pittsburgh, Pittsburgh, PA (US)

( * ) Notice: Subject to any disclaimer, the term of this patent is extended or adjusted under 35 U.S.C. 154(b) by 1504 days.

(21) Appl. No.: 11/155,875

(22) Filed: Jun. 17, 2005

(65) Prior Publication Data

US 2005/0283068 A1    Dec. 22, 2005

Related U.S. Application Data

(60) Provisional application No. 60/580,513, filed on Jun. 17, 2004.

(51) Int. Cl.
*A61B 5/05* (2006.01)
(52) U.S. Cl. .......................................... 600/410; 324/306
(58) Field of Classification Search .................. 600/407, 600/408, 410–423; 324/306–309, 318–322
See application file for complete search history.

(56) References Cited

U.S. PATENT DOCUMENTS

| | | |
|---|---|---|
| 4,466,075 A | 8/1984 | Groch et al. |
| 5,080,100 A | 1/1992 | Trotel |
| 5,103,823 A | 4/1992 | Acharya et al. |
| 5,214,711 A | 5/1993 | Neely et al. |
| 5,295,483 A | 3/1994 | Nowacki et al. |
| 5,389,101 A | 2/1995 | Heilbrun et al. |
| 5,398,684 A | 3/1995 | Hardy |
| 5,412,419 A * | 5/1995 | Ziarati .............................. 348/61 |
| 5,414,459 A * | 5/1995 | Bullwinkel ..................... 348/53 |
| 5,427,102 A * | 6/1995 | Shimode et al. .............. 600/410 |
| 5,446,548 A | 8/1995 | Gerig et al. |
| 5,482,042 A | 1/1996 | Fujita |
| 5,558,430 A | 9/1996 | Booty, Jr. |
| 5,727,554 A | 3/1998 | Kalend et al. |
| 5,877,732 A * | 3/1999 | Ziarati .............................. 345/8 |
| 6,144,875 A | 11/2000 | Schweikard et al. |
| 6,279,579 B1 | 8/2001 | Riaziat et al. |
| 6,501,981 B1 | 12/2002 | Schweikard et al. |
| 6,540,679 B2 | 4/2003 | Slayton et al. |
| 6,621,889 B1 | 9/2003 | Mostafavi |
| 6,662,036 B2 * | 12/2003 | Cosman ........................ 600/411 |
| 6,690,965 B1 | 2/2004 | Riaziat et al. |
| 6,731,970 B2 | 5/2004 | Schlossbauer et al. |

(Continued)

*Primary Examiner* — Brian Casler
*Assistant Examiner* — Nasir S Shahrestani
(74) *Attorney, Agent, or Firm* — Blynn L. Shideler; Krisanne Shideler; BLK Law Group

(57) ABSTRACT

Critical needs for MRI patient instruction, testing, comfort, motion control, and speech communication are provided for better imaging which leads to more effective medical care. An MRI Digital Video Projection System is disclosed which provides better quality display to the patient to better inform, instruct, test, and comfort the patient plus the potential to stimulate the brain with microsecond onset times to better diagnose brain function. An MRI Motion Tracker and Patient Augmented Visual Feedback System enables monitoring patient body part motion, providing real time feedback to the patient and/or technician to substantially improve diagnostic yield of scanning sessions, particularly for children and mentally challenged individuals. An MR Forward Predictive Noise Canceling Microphone System removes the intense MRI acoustic noise improving patient communication, patient safety and enabling coding of speech output. These systems can be used individually but maximum benefit is from providing all three.

14 Claims, 7 Drawing Sheets

U.S. PATENT DOCUMENTS

| | | | |
|---|---|---|---|
| 6,774,929 B1 * | 8/2004 | Kopp | 348/61 |
| 6,778,850 B1 | 8/2004 | Adler et al. | |
| 6,865,253 B2 | 3/2005 | Blumhofer et al. | |
| 6,937,696 B1 | 8/2005 | Mostafavi | |
| 2003/0071624 A1 * | 4/2003 | Schwarz | 324/318 |
| 2004/0193413 A1 * | 9/2004 | Wilson et al. | 704/243 |
| 2005/0047611 A1 * | 3/2005 | Mao | 381/94.7 |

* cited by examiner

MAGNETIC RESONANCE IMAGING HAVING PATIENT VIDEO, MICROPHONE AND MOTION TRACKING

RELATED APPLICATION

This application claims the benefit of U.S. provisional patent application Ser. No. 60/580,513 entitled "Patient Video Feed, Patient Microphone and Patient Motion Tracking in MRI" filed Jun. 17, 2004.

BACKGROUND OF THE INVENTION

1. Field of the Invention

This invention relates to products used in MRI imaging, specifically providing systems to provide high speed digital video images to the MRI system patient, collect speech data from the MRI system patient and to track and to minimize patient movement within the MRI system. These systems enhance patient cooperation to improve the quality of scanner data collection. The innovations of the present invention will enhance diagnostic effectiveness of MRI imaging, patient comfort, patient safety, and will lower MRI imaging costs.

2. Background Information

Magnetic Resonance Imaging (MRI) allows research and diagnostic imaging of humans and animals. An MRI provides two and three dimensional imaging of internal tissue, and can provide imaging of functioning processes of tissue called Functional MRI or fMRI. MRI involves using a combination of high strength magnetic fields and brief radio frequency pulses to image tissue, typically by imaging the dipole movement/spin of hydrogen protons.

MRI is typically performed in a large magnet in which the patient is confined within a narrow bore. The imaging process typically involves the patient being subjected to loud sounds and vibrations in a very confined space. For clear imaging it is typically required that the patient remain very still, not moving more than a few millimeters over a period of minutes or even hours. Some MRI patients perceive this as a high anxiety inducing environment. It is difficult for patients to remain still, be entertained, be pacified, and communicate in this environment.

There is a great need in the MRI field for systems that can assist the patients in being motionless, can assist the patients in communicating with the technologist, can assist in calming the patients, can assist in entertaining and providing other feedback and desired stimulus to the patients.

These systems or innovations can substantially improve the nature of human MRI imaging and can substantially improve diagnostic effectiveness of such imaging. As noted above, in order to obtain an acceptable or good scan the patient must not move for extended periods of time. It has been estimated that this is a serious problem for over 20% of the MRI patients. Furthermore, with children as MRI patients the yield of effective scans can be below 20%, when using standard MRI methods. Implementing improved systems for providing instructions, feedback, and entertainment, tracking movement, and hearing the patient are believed to increase the yield of acceptable scans to over 90%, making diagnosis and medical treatment more effective. These types of MRI imaging support systems or tools can also provide added safety benefits to the MRI system. An effective MRI patient microphone system would allow the operator to hear comments by the patient during scanning even if they are spoken in a low or modest volume (in contrast to current microphone systems that would generally require a patient to yell to be heard making them in-effective). Another safety benefit of these proposed systems is that the tracking of movement by the patient in real time can alert the operator to signs of patient distress that can be checked out in a timely fashion prior to the patient's condition deteriorating further. This data can also be used by the technician/technologist to assess whether patient movements have been so significant so as to warrant the halt and restart of the scanning session.

The MRI environment requires unique approaches to solving problems due to the high magnetic and radio frequency characteristics of MRI imaging. There are three design challenges that must be overcome in implementing any MRI system. First the MRI involves a very intense magnetic field and intense RF emissions that disrupt common electronics (e.g., transformers and coils). Second MRI requires the devices to show very low ferromagnetic properties (so they are not attracted into the magnetic field or disrupt the homogeneity of that field). Third MRI requires devices to show very low EMF emissions which increase the RF noise of MRI imaging and reduces the quality of the imaging. Specialized devices must be built to operate in this environment.

The present invention integrates three devices or systems in an MRI environment for solving critical needs for MRI patient communication/comfort, control, and safety. The first system is an MRI Digital Video Projection System, the second system is an MRI Motion Tracker and Patient Augmented Feedback System and the third system is an MRI Forward Predictive Noise Canceling Microphone System. The details of these systems and the integration of these systems into an MRI environment are discussed in detail below. The advantages of these individual systems will be clarified by an examination of the background for each system.

MRI Digital Video Projection System. In an MRI environment there are a number of reasons to provide the MRI patient with a video image. There have been a variety of video projection systems for MRI environments to accomplish this. There are four video projection methods currently in use, namely: a) filtered video, b) shielded video, c) fiber optic image projection, and d) projected video. In filtered video, as discussed in U.S. Pat. Nos. 5,076,275, 5,877,732 and 5,432,544, the video passes through a low pass RF filter to eliminate video signals above about 30 MHz. The MRI signal operates at high frequencies typically greater than 64 MHz. The problem with this approach is current computer video displays have signals of much higher frequencies (e.g., 1.65 Gb/s for DVI) and harmonics that pass through the range of frequencies that an MRI recording is very sensitive to. This makes the filtered solution ineffective for many video displays. Shielded video, as described in U.S. Pat. Nos. 5,861,865 and 5,864,331, can shield high frequency signals that pass into the MRI room. However, shielded wire can not sustain the very high frequencies of current generation digital displays over the distances, typically tens of meters, involved between the video/computer device and the video display device in a conventional MRI environment. Fiber optic image projection systems, as described in U.S. Pat. Nos. 4,901,141 and 5,414,459, send the video image from and LCD type display some distance from the magnet through fiber optic bundles (such as in bore scopes). However these bundles are very costly and suffer from fiber drop out causing lost pixels and poor image quality. Past projections systems for MRI environments, such as described in U.S. Pat. No. 5,076,275, have provided CRT or LCD projections which provide an analogue display system. These have projected the image outside of the MRI bore resulting visual images that include extraneous distracting visual information and often do not show the display image due to having part of it obstructed either by a body part or the magnet bore. The LCD systems typically have a problem with slow pixel rise time (e.g., 30 ms rise time) smearing the video for rapidly changing displays and suffering from analog distortion of the video image.

MRI Motion Tracker and Patient Augmented Feedback. In MRI imaging it is critical to minimize body motion during the period of scanning, typically 20-180 minutes, that occurs in the acquisition of the images. This is particularly true regarding head movement for MRI brain imaging. A body part moving in the scanner will change the position of the body tissue, with the change of tissue position substantially degrading the image quality. The body in the magnetic field distorts the uniformity causing variation of the MRI signal return and reconstruction error. There are methods for post processing motion correction (e.g., use of AIR algorithms) but these provide only a partial correction (e.g., operate when motion is less than 5 mm of movement). Many methods have been employed in an attempt to achieve head stabilization: surgical pillows, head vices, bolting of heads, bite bars and use of parallax displays. All of these approaches are unsatisfactory principally because patients do not respond well (e.g., concern about gagging when using bite bars) or they become painful (e.g., head vice) resulting in more movement from the pain or interfere with the task (e.g., visually watching a parallax of multiple points). Techniques have been adapted to optically track surgical instruments in MRI for surgery planning, such as described in U.S. Pat. No. 5,603,318. However these MRI environment tracking techniques are poorly suited for tracking body parts and provide no feedback to minimize movement. Most patients in an MRI environment wish to be compliant. However it is nearly impossible for the patient to sense small movements (1 mm, 1° rotation) of the body part, particularly if they occur over a period of time (e.g., head nodding 0.1° per minute during the course of an hour). What is needed is effective sensing of the movement and augmented feedback to the patient and technician to enable minimizing movement.

MR Forward Predictive Noise Canceling Microphone. There have been a variety of microphone systems in use in an MRI environment. Some of these include sound cancellation, such as described in U.S. Pat. Nos. 5,313,945 and 5,427,102. These existing systems use a method of concurrent noise cancellation in which one microphone is placed to input the noise and a second to input the patient speech and noise. Cancellation is accomplished by subtracting the alleged "noise only" microphone signal from the alleged "speech and noise" microphone signal thereby yielding a speech only signal. However this approach depends on multiple microphones having equivalent sound sampling of the noise and differential sampling of the speech. This can only be approximated because the microphones differ in their response to auditory input and their placement resulting in differential phase and amplitude recording of both the speech and noise.

An object of the present invention is to provide an MRI having systems that can assist the patients in being motionless, can assist the patients in communicating with the technologist, can assist in calming the patients, can assist in entertaining and providing other feedback and desired stimulus to the patients. An MRI which has such systems or innovations can substantially improve the nature of human MRI imaging and can substantially improve diagnostic effectiveness.

SUMMARY OF THE INVENTION

At least some of the above stated objects are achieved with an MRI device according to the present invention. The MRI device or system according to the present invention includes three MRI systems (or sub-systems), namely an MRI digital video projection system, an MRI motion tracker and patient augmented visual feedback system, and an MRI forward predictive noise canceling microphone system. The first system is an MRI Digital Video Projection System which uses a combination of digital video and digital components to provide high speed, precise digital video in an MRI magnet without introducing any RF noise. The second system is an MRI Motion Tracker and Patient Augmented Visual Feedback System that enables monitoring patient head motion (or any body part motion) and providing real time feedback to the patient and/or technician or technologist to minimize patient movement. The third system is an MRI Forward Predictive Noise Canceling Microphone system which provides a system and method that effectively removes the intense MRI acoustic noise produced during scanning by the magnet through the use of predicting the repeating signal of the MRI magnet (i.e. the noise) and canceling that acoustic noise signal leaving essentially only the patient's speech. The purpose of this invention is to solve critical needs for MRI patient communication/comfort, movement control, and speech communication. This will increase the diagnostic quality of the imaging (e.g., by reducing movement and better task control of brain activation), patient comfort (by providing distraction), and patient safety (making low volume speech understandable during the scan).

The MRI Digital Video Projection System involves providing digital video from a computer or digital video source projected into the magnet system. The present invention is an all digital solution including using the Digital Video Interface (DVI) from a computer or video device, a fiber optic DVI to fiber optic converter, a digital fiber optic cable, an optical to DVI converter, a Digital Light Processing (DLP) projector, specialty lenses to project the DVI image, and RF shielding and power signal filtering to limit the DLP projector EMF signals from interfering with the magnet or the magnet interfering with the DLP projector. Additionally, there is a screen viewable by the MRI patient, such as a rear projection screen, onto which the image may be projected. A prism or mirrors may be provided as needed to enable the patient to see the projected image. This system has the advantages of: being all digital and thereby preserving the quality of the image; using fiber optic transmission of signals thereby eliminating the potential of the cable bringing in or emitting radio signals that would distort the imaging process; using digital high speed DLP technology to enable very fast (microsecond rise time) displays showing better dynamic displays and enabling precise stimulation of the patient for brain mapping.

The MRI Motion Tracker and Patient Augmented Feedback System according to the present invention precisely monitors body part motion in an MRI environment, operates in the confined space of the magnet, and is not effected by and does not effect the MRI scanning operation, neither magnetically, electrically, or mechanically. This system involves monitoring body part movement and projecting that movement in up to six degrees of freedom (X, Y, Z, yaw, pitch, roll), or some reduced degrees of freedom, visually, and/or audibly, back to the patient and/or to the technician (or operator or technologist) to aid the patient in understanding and reducing movement. A typical example of use of this system would be monitoring head motion of an MRI patient during brain imaging. A significant part of this system is the use of an augmented virtual display projected to the patient and/or technologist during the scanning session to provide control and highlighting of the feedback to the patient (directly or via the technologist) to reduce movement. The visual feedback can optionally be enhanced with, or possibly replaced by, corresponding auditory feedback. For example, at the beginning of an MRI run there would be a display showing movement of the patient body part relative to the desired location. The patient would be given instruction on how to move the body part to return it to the desired location. During a scanning run the patient could be provided the movement displays to help them minimize movement. In some scanning, such as functional MRI scanning (fMRI), the patient must perform some task during the scanning and may not be able to monitor the movement during the run. In those cases the augmented display of movement can be discontinued for the patient (but provided to the technologist running the scan), or equivalent auditory feedback could be provided. At the end of the run the patient and technologist can review the movement track to help the patient understand and minimize future undesired movement. The display to the patient and technologist could be via a computer display showing graphically the movement, distance from the desired position of the body part, and position indicators for the body part (e.g., display of traffic light signal of green (good part location), yellow (warning) and red (bad) movement behavior).

The system provides a combination of camera based optical motion capture mechanism with a computer display for the technician and/or patient in real, or delayed time, to provide the patient augmented feedback as to head (or other body part) position. In the case of head motion, this invention tracks the head motion and displays to the patient and/or the operator the position of the head to enable the patient to return/maintain the desired location (optional auditory feedback may be provided as well in place of or supplementing the visual feedback). The preferred implementation tracks a target attached to the patient's body part providing six degree of freedom (6D) representation of the position. The position and movement may be displayed in a variety of graphic representations. Typically at the beginning of a run, or scan, the patient will be requested to return the body part to a desired or target location. During the scanning, the patient could optionally be shown the movement and asked to maintain the desired or target position. Alternatively the data would be recorded. At the end of the run the patient can be provided feedback indicating if the movement was acceptable and displays of movement trajectory in 1D, 2D rotation (head nodding, shaking), 3D position (x,y,z), 3D rotation (nodding, shaking, tilting), and 6D movement. The use of motion tracking in the magnet and providing the augmented computer synthesized feedback to the patient to allow them to learn to hold their body part still and to return to a given location or to review past movement events can substantially increase the yield of successful MRI imaging.

The motion tracker can also be used to improve the imaging of the scanner. New scanner acquisition options such as the Siemens Prospective Acquisition Correction (PACE) provide methods for the scanner to partially correct for motion by reorienting the gradients to track the movements while collecting images. These methods typically suffer because they have difficulty determining position fast enough to apply the movement (e.g., it may take 4 seconds to detect the movement and during that period the wrong movement correction is being applied that distorts the image relative to the "uncorrected image"). The current system can provide accurate movement detection in milliseconds allowing precise tracking of the movement and will enable better scanner gradient adjustments to track the movement.

The MR Forward Predictive Noise Canceling Microphone System provides a system and method to remove the MRI acoustic noise from the patient microphone to enable the technician or technologist to hear clear speech in the presence of very intense (the equivalent of jet engine sound level, 130 db SPL) MRI magnet presented noise. This is important for patient safety and for viable communication between the technologist and the patient. For example, an anxious patient may forget to press an emergency button, or may quietly indicate their distress which would not be acoustically distinguishable by the technologist. In addition, for some brain imaging procedures using fMRI methods, it is important to verify that the subject is performing the task. Using speech output allows tracking the verbal behavior of the patient. Nearly all MRI scanning involves a repetitive recording in which multiple slices/volumes are re-sampled over a short period referred to as a TR (time to recovery) repeating the signal to over a short period of time (typically 0.1 to 4 seconds). These MRI sound effects are acoustically repetitive (see Ravicz M E, Melcher Jr, Kiang N Y, "Acoustic Noise during Functional Magnetic Resonance Imaging", J. Acoustic Soc. Am. 2000, Vol. 108 Pgs 1683-1696). The present invention uses this repetitive nature to enable cancellation using a previously recorded sample from the same microphone to cancel the noise. The system cancels the noise utilizing the repetitive nature of the MRI noise signal to remove the reoccurring noise. The system uses a single microphone to record both the "noise" and the "noise and speech". The system tracks the repetitive nature of the MRI noise either by getting an input from the task computer, scanner, or technologist, of when the sound should repeat, or by examining the acoustic signal and determining its repeat interval. In addition, it is provided input from at least one of the technologist, patient, MRI control system, or microphone as to whether the patient is speaking. During times that the patient is assessed as not speaking, the system records a digital waveform of the expected sound signal received by the microphone. This wave form, or template, is then subtracted from subsequent input waveforms to provide a signal with sharply reduced MRI acoustic noise. The template is adaptive and is updated during any time that the patient is not speaking. The difference, or error signal, between the input waveform and the subtracted waveform or template is tracked. If the difference is above a preset threshold, or amplitude, the patient is presumed to be speaking. The technologist may be provided with a signal indicating the patient is speaking (e.g. an indicator light or warning alarm to draw attention of the technologist). When the patient is presumed not to be speaking the template is updated to provide an updated, recent template for subsequent noise cancellation purposes. This enables the system to easily adapt to small patient movements (e.g., hand movement during a scan) that alter the acoustic environment during the scanning. At the end of the scan the noise cancellation is stopped (so as not to produce noise when the scanner stops acquiring images). The end result is a very high signal to noise speech signal of the patient speaking during the scan.

In the present invention noise cancellation microphone system there is no problem with differential microphone placement, sampling of the sound environment, or matching of microphones, and these factors provide substantially better noise cancellation than prior art systems and do so at reduced cost. As noted above the present system is able to distinguish between when the signal from the microphone is signal and noise or noise alone. The present invention accomplishes this in two methods. First informed signal processing is utilized in which a signal from the operator console, computer running the task and/or the patient is provided indicating a time when there is an expectation that the patient would be talking. Second, as discussed above, a recent template comparison technique is used comparing the input signal to a recent sample and determine if it is likely to be noise alone or noise plus speech based on match to the past noise signal. If it is noise alone, then it is used as the template for the next period of scanning. A validation of "the recent template" approach was performed in 2004 and is described in a manuscript written by Kwan-Jin Jung entitled "Extraction of Overt Verbal Response From the Acoustic Noise in a Functional Magnetic Resonance Imaging Scan by Use of Segmented Active Noise Cancellation" and published in 2005 in Magnetic Resonance in Medicine, Volume 53 Pages 739-744. The recent template technique adapts to small patient movements in the magnet (e.g., if the person moves their hand in the magnet that alters the acoustic environment and hence reduces the quality of the noise cancellation). By using the noise recorded during the previous TR, the system can adapt the cancellation to compensate for patient movement to keep the quality of noise cancellation high. The combination of forward cancellation with information about the likelihood of speaking provides a cost effective system and methodology that allows very clear speaking of the individual to be heard in an MRI environment.

These and other advantages of the present invention will be clarified in the following description of the preferred embodiments together with the attached figures in which like reference numeral represent like elements throughout.

BRIEF DESCRIPTION OF THE DRAWINGS

The accompanying drawings, which are incorporated in, and form a part of, the specification, illustrate preferred embodiments of the present invention and, together with the description, serve to explain the principles of the invention, and are not intended to be restrictive thereof. The drawings are not necessarily to scale, emphasis instead being placed upon clearly illustrating the principles of the invention. In the drawings.

DETAILED DESCRIPTION OF THE PREFERRED EMBODIMENTS

Figure 1:
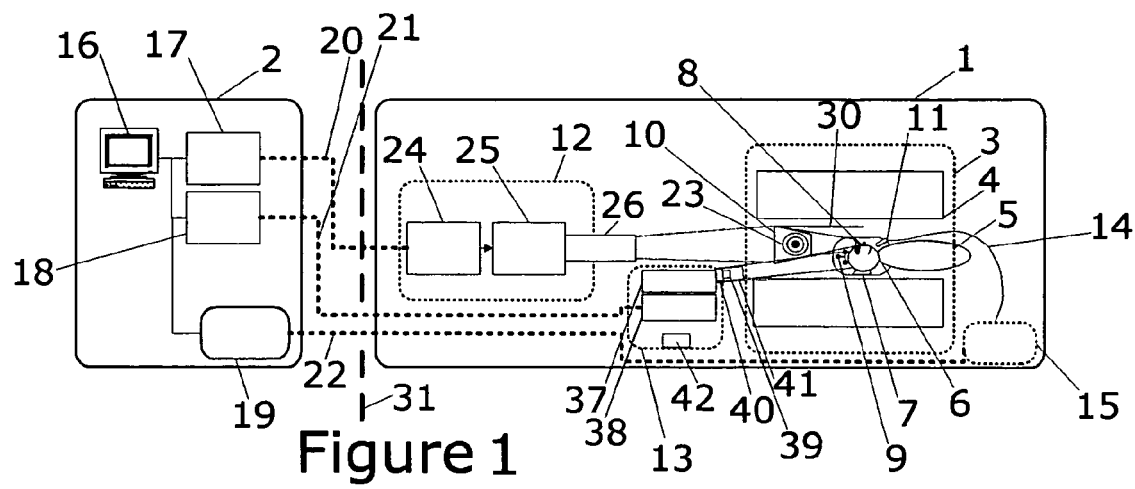
FIG. 1 is a schematic view of the general configuration of the components in the MRI magnet environment according to the present invention, and illustrating the division of components in the magnet room 1 and control room 2.
Figure 2:
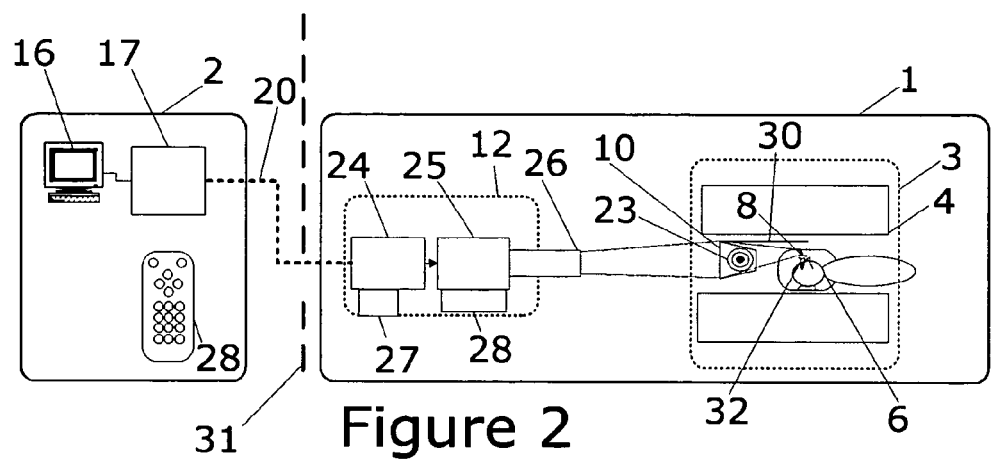
FIG. 2 is a schematic view of the general configuration of the digital video patient display components according to the present invention.

Reference will now be made in detail to the preferred embodiment of the invention. FIG. 1 provides to overview of all the components of the MRI system according to the present invention. The three sub-systems of the MRI system according to the present invention include a digital projection system, a movement monitoring system, and a microphone system can be used together, in other in combinations or individually. The equipment involves conventional components in the MRI magnet room 1 and the MRI control room 2, which components need not be discussed in detail herein. All signals pass through digital fiber optic cables (20, 21 and 22) through a penetration panel or wave guide 31.

The MRI Digital Video Projection System of the present invention is shown in FIG. 1-5. The system includes a viewable rear projection screen 23 that a patient can see typically by viewing it after the image is reflected from a mirror or prism 8. Other projection surfaces (e.g. front projection screen) can be used provided they are viewable by the patient. If the patient requires vision correction, they may view the display through glasses 32. The video, or scene or image viewed by the patient, may include material such as instructions, entertainment, brain activation tasks, and feedback of performance and movement. The image is projected by a digital projection device such as a Digital Light Processing (DLP) 25. Other projector technologies could be used. However, the preferred embodiment is a DLP projector 25 because it provides microsecond rise time intensification of the display, and maintains digital image quality.

DLP projectors are commercially available in one DMD chip and three DMD chip models. In a three DMD chip projector, each color (red, green, and blue) has its own dedicated DMD chip and the output frame rate is generally considered synchronous with the incoming video signal refresh rate. In a single DMD chip projector, a color wheel containing red, green, and blue color filter segments is placed between the light source and the DMD chip. The DMD control electronics are timed so each mirror is directing the light into or away from the projection lens for each passing color segment of the color wheel, as determined by the RGB color data decoded from the incoming video signal. Since the color wheel spins at a fixed frequency, the display electronics scale the incoming refresh rate to a fixed frequency (typically 60 Hz), causing the output frame rate to be asynchronous relative to the vertical refresh rate of the incoming video signal. For many general projector applications the asynchronous operation of the single DMD chip projector is of little or no consequence; however applications such as stereo projection and the presentation of visual stimuli during human behavioral research require precise synchronization. In many psychophysical experiments, millisecond precise stimulus durations are required to achieve accurate data collection and analysis. In a non-synchronized system, the PC will typically be sending video frames at a faster rate than the projection device can display. This will cause missed frames and image tearing resulting in extremely inaccurate stimulus durations that may go entirely undetected by a researcher who is unaware of the synchronization capabilities of the device. Even if the refresh rates of the two devices are closely related (i.e. 60.1 Hz and 59.9 Hz) the small time difference will cumulate resulting in an increasing error as time progresses. A three DMD chip projector may be used to achieve synchronization but is impractical for most users because, on average, they increase cost and weight by 10 times that of the single DMD chip projectors. The present invention allows the use of a single DMD chip DLP projector 25 by providing synchronizing unit for the single DMD chip DLP projector. The synchronizing unit of the present invention uses a signal obtained from the rotation of the color wheel as a frame synchronization input to a video card capable of supporting "genlock" or frame synchronization, such as the NVIDIA Quadro FX 3000G. The color wheel signal is always an exact multiple of the projected frame rate and may be obtained optically by placing one end of a fiber optic cable near the output of the color wheel and the other end in a photo-receiver device, or electrically by using an existing electrical signal that is controlling the color wheel. The obtained color wheel signal is then be sent back to the video card's genlock input via optical or electrical cabling allowing it to be used inside or outside of the shielded MRI room 2.

It is critical for the projector 25 in the MRI environment of the magnet room 2 to not emit radio frequencies (RF) that interfere with the MRI magnet 3. The projector 25 would be in a Faraday cage 12 for the projector 25. The cage 12 provides a high degree of RF shielding. The Faraday cage 12 may also shield the projector 25 from the magnetic field of the magnet 3 by, optionally, including some ferrous materials in the walls of the RF cage 12. This can only be done if the projector 25 is sufficiently away from the magnet 3 not to disturb the homogeneity of the magnet field (e.g., over 2 meters). To provide an effective RF cage 25, all power and holes must be sealed, as is known in the art, either with conductive surfaces or with wave guides. Further, the power supply will have filters to minimize any entry or exit of RF on the power AC input cords. A fan 28 of the projector 25 would have a conductive shield or screen to shield RF emissions. The lenses of the projector 25 would be placed within the wave guide of the cage 12. The wave guide 12 would block RF above 50 MHz. There is no RF filtering of the data signals coming into the Faraday cage 12. The projector 25 electronics would be expected to emit high frequency RF noise which will be blocked from exit by the Faraday cage 12.

Figure 3A:
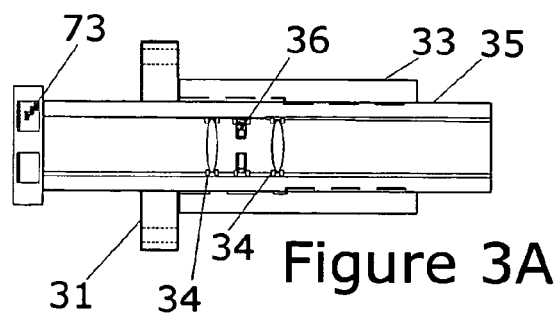
FIG. 3a is a schematic view of the projection lens system and wave guide according to one embodiment of the present invention.
Figure 3C:
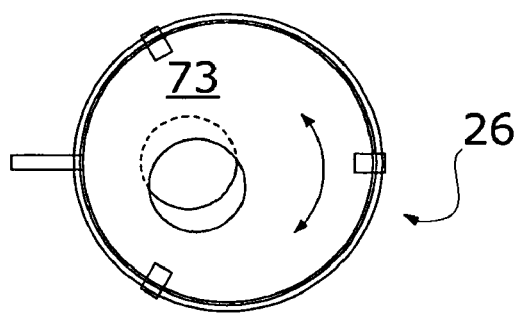
FIG. 3c is a front schematic view of a variable aperture for the projection lens system and wave guide of FIG. 3b.
Figure 3B:
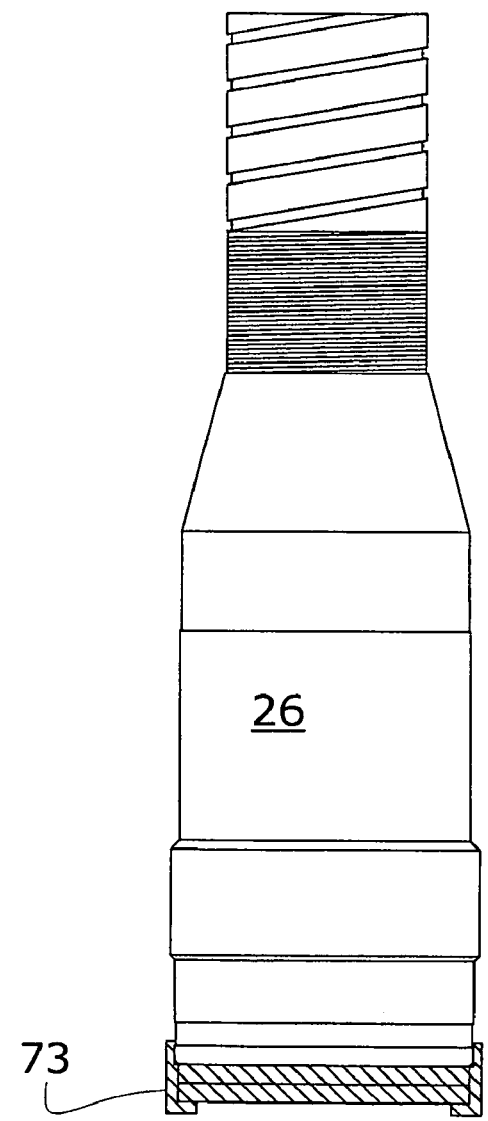
FIG. 3b is a schematic view of the zoom type projection lens system and wave guide according to one embodiment of the present invention.

One of the most critical capabilities that distinguish an MRI projection system from a standard off-the-shelf projector is its ability to project a small image at relatively long throw distances. The system includes an additional lens system 26 that would act as part of a wave guide and project a small image at a distance. Lenses of the lens system 26 projecting in the MRI magnet room 2 contrasts with the lens of standard DLP projectors. Standard projectors 25 typically seek to magnify the image such that at short distance there is a large image (e.g., at a distance of 3 meters have an image of 3 meters). In the MRI magnet room 2, the image is constrained by the size of the magnetic bore and typically the projection would require a size of 0.3 meters at 3 meters distance. This requires a longer focal length lens system 26. There is a need to get a clear projected image so it is preferred not to put a screen or glass type RF window to limit RF emissions, though they could be used. The preferred embodiment includes a lens system 26 that also acts as a waveguide. That is there is a tubular wave guide sufficiently long enough to block RF frequencies (e.g., at 30 cm length for a 5 cm inside diameter). There are two different types of projection lens systems 26 available in this invention, a fixed focal length (FFL) lens (FIG. 3a) and a zoom lens (FIG. 3b). The FFL lens 26 provides a relatively simple, inexpensive solution for applications where the projector 25 can be physically moved to the proper position for desired image size and where focus is the only desired image adjustment. The zoom lens 26 (FIG. 3b) provides the capability of quickly placing the projector 25 in a desired location and moving the zoom and focus adjustments on the lens for a desired image size. For use in the MRI magnet room, the outer shell of both lenses are electrically mated to the Faraday cage allowing it to function as a waveguide having sufficient length and diameter to achieve an RF attenuation of at least 65 db at 50 MHz. The lenses may also be constructed using a non-conductive housing and operated inside a waveguide of sufficient length and diameter to achieve the above-mentioned attenuation with the waveguide electrically bonded to the Faraday cage. The lenses of the lens system 26 are designed to move along the inside of the tube in the zoom lens configuration. The lens system 26 does not compromise the wave guide due to either (1) being non-conductive or (2) being connected to the wave guide with sufficient conductivity contact to still provide a wave guide of sufficient length to block the high frequencies emitted by the projector. The lens system 26, as shown in FIG. 3a includes the wave guide/lens tube 33, lens positioning unit 35 (either a threaded tube or a sliding tube) and lens 34 with optional aperture control 73 to sharpen the image and control light output. There may be an optional light baffle 36 to reduce extraneous light and improve image homogeneity (the light baffle can be fixed for fixed focal length lens systems 26). The wave guide/lens tube 33 is bolted to the projector RF cage 12 to make a low impedance electrical contact and to minimize EMF emissions. The lens system 26, as shown in FIG. 3b, also includes the wave guide/lens tube 33, lens positioning unit 35 (either a threaded tube or a sliding tube) and lens 34 with aperture control 73 (shown in FIG. 3c) to sharpen the image and control light output. Further, the zoom lens system 26 of FIG. 3b will have the ability to change the relative distances between the lenses 34 within the wave guide in a manner known in zoom lens construction. The aperture control 73 is an adjustable Elliptical Iris which provides the capability of decreasing the brightness of the projected image. This may be necessary when the viewer and the semitransparent projection screen are in direct line of sight with the projectors high-intensity light output. The elliptical iris also helps to decrease the effect of any optical system aberrations thereby improving image contrast, clarity, and focus. The lens system 26 in either the fixed or zoom version is completely nonferrous and snaps onto the front of the zoom lens.

The signal input to the projector 25 would occur via fiber optic input. The video signal is a digital video input such as a Digital Video Interface (DVI input developed by the digital display working group http://www.ddwg.org/). The DVI technology has very high frequency bandwidth (i.e., 1.65 Gb/s), so high it makes it impractical to use RF filtering on the line to stop RF spectrum emissions from being carried on the cable (as utilized by previous technologies such as in U.S. Pat. Nos. 5,076,275, 5,877,732 and 5,432,544). It is also difficult to transmit such bandwidth over wire over the extended distances between the control room 2 and the projector 25 (more then 10 meters). To solve these problems we take the output from the task computer or video device 16, convert the DVI signal electrical signal to digital optical signals at converter 17, transmit the data via optical fiber 20 to a Digital Optical to DVI converter 24 which is connected to the projector 25. In addition to the video signal, control signals for the projector 25 remote control (e.g., power up/down, projection modes) is provided by the standard projector remote 28 inputting to an IR detector being transmitted via the optical fiber 20 and the fiber 20 being placed near the projector 25 IR remote sensor. Likewise status signals originating from the projector are transmitted to the control room via either fiber optic or wire connections (e.g. power up in progress, projector ready, overheated—offline, lamp malfunction—offline, no power, whether the projector is in synch or not (as described above), etc).

Figure 4:
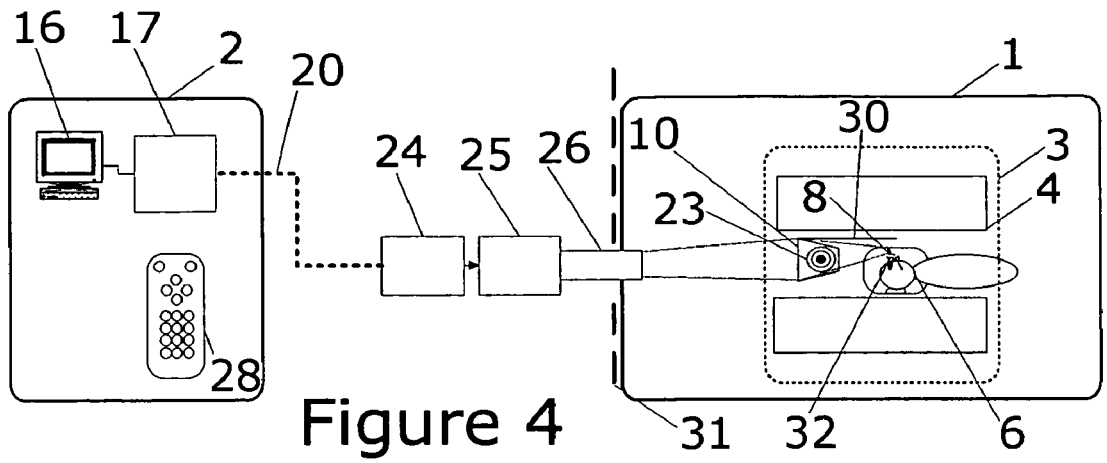
FIG. 4 illustrates a use of the projector according to the present invention outside of an MR room.
Figure 5:
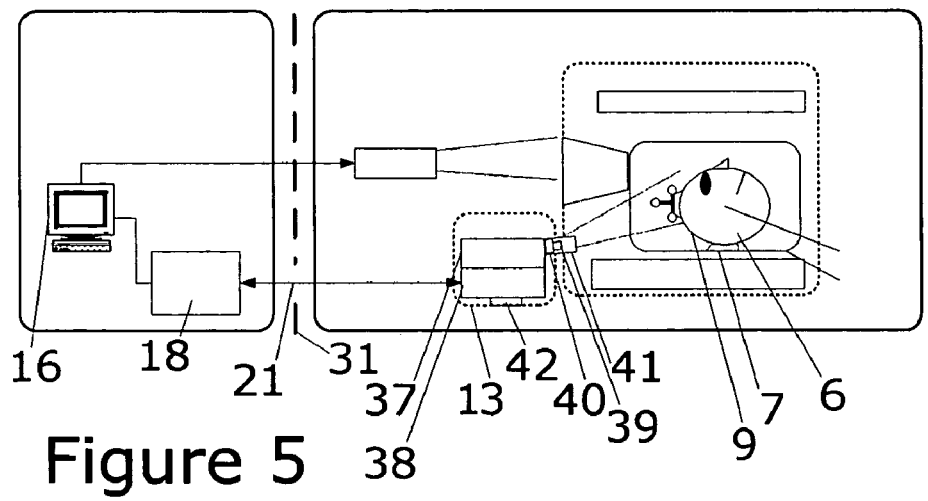
FIG. 5 is a schematic view of the general configuration of the movement monitoring system components according to the present invention.

FIG. 4 Shows the configuration for the exterior room version of the projection system. Some MRI magnet rooms 1 are built providing a waveguide for projection installed into the MRI magnet. This has the disadvantage of requiring more room site constraints (e.g., the distance to the back wall of the room and position of the wave guide but has the advantage of providing shielding). In this case the Faraday shielding 12 is not necessary because the room shield provides the shielding.

The MRI Motion Tracker and Patient Augmented Feedback system is shown in FIG. 1 and FIG. 5-9. The preferred embodiment involves the patient wearing a visible movement target 9 of infrared (1R) reflectors on the head, such as either on a small cap, or directly on the head, or on the end points of the imaged body part (e.g., joints of an arm). These are imaged with a high resolution camera 37 with an IR emitting source 40 and the camera lens 39 both of which pass light through an opening in a tubular wave guide 41. The preferred implementation would use a USB camera and have a USB to fiber optic converter device 38. Alternative implementations could use other video camera and conversion cables such as NTSC to fiber converters. The camera electronics are enclosed in a Faraday cage 13, such as cage 12 described above that blocks RF above 50 MHz. The power input is passed through an RF filter 75. In alternative implementations the camera could have a telephoto lens and be placed outside of the magnet room (similar to the projector in FIG. 3).

The patient would typically utilize some support structure 7 that would limit movement of the to-be-imaged body part to a small number of dimensions and limited but not completely retrain movement. For example a cup like head support 7 would limit the X, Y, Z position of the back of the head. The patient could still rotate the head in various directions (head nod, shake, and tilt). These movements would typically be reduced by pads or pillow to constrain the head direction. However, to minimize pain, the compression of the head needs to be limited, so typically the backing or support 7 is more of a guide than a fixed barrier to movement. As noted above, pain induces movement and causes patients to discontinue scanning defeating the value of constraining the movement in this way. Even modest compression over an hour can become painful. Using a pad or support 7 to limit movement does aid the patient in keeping the head close to the desired position and limiting the number of movement directions to those that can be interpreted easily (e.g., nod the head up or turn right). It also reduces the dimensions of movement that need to be displayed and interpreted by the patient. This aids the patient to know how to interpret and correct any movement.

A fiber optic cable 21 feeds the camera 37 signal into the control room 2 to an optical to USB converter 18 in the control room feeding the signal to the processing computer 16. The computer processes the video data, displays movement data to the operator and to the patient via the projection system (such as discussed above).

Figure 6:
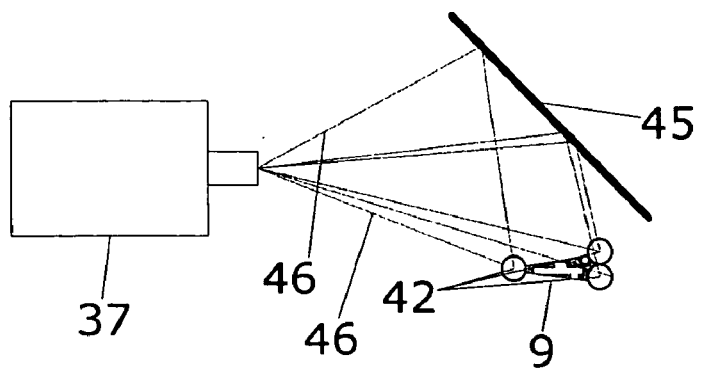
FIG. 6 is a schematic plan view of the motion camera and target for the movement monitoring system of FIG. 5.

FIG. 6 shows the top view of the camera imaging the target for the IR target 9. The camera 37 would take an image of the patients head with the video target 9 directly and through a mirror 45 of the position. The direct image would return the horizontal and vertical position of each IR sphere of the target 9, the image of the reflected image from the mirror 45 would provide the depth and vertical position of each sphere of the target 9. With this data the location of each sphere of the target 9 can be determined. Note the imaging of 3 points allows the software to assess accuracy of the positions (e.g., points A, B are determined of a triangle, the point C can be predicted). Any difference between the predicted C point and the observed point is error. Alternatively there can be a least squares fit to all 3 points to reduce error. As opposed to using one camera 37 with a reflected image, multiple cameras can be used without the need of the mirror 45.

Figure 7:
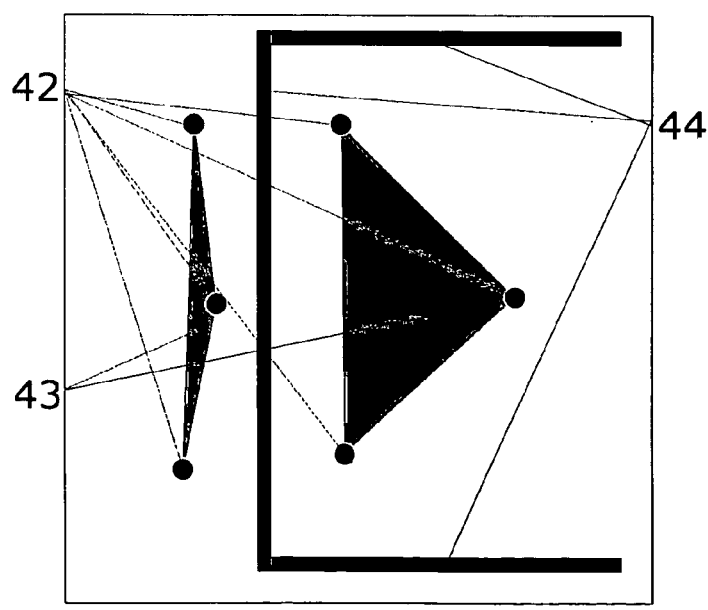
FIG. 7 is a view of a sample processed image of target in movement tracking.

FIG. 7 shows the sample video of a high contrast image. The spheres 42 of the target 9 are nearly round and of high reflective intensity. The round image allows sub pixel resolution of the center of mass of each sphere 42. The mirror 45 would have a border of IR reflective tape 44 allowing determination of the mirror 45 borders and clear delineation of what sphere images are reflected versus direct images. Note many options would allow accurate motion capture (e.g., two spheres could be used since the movement of the head is typically constrained).

Figure 8:
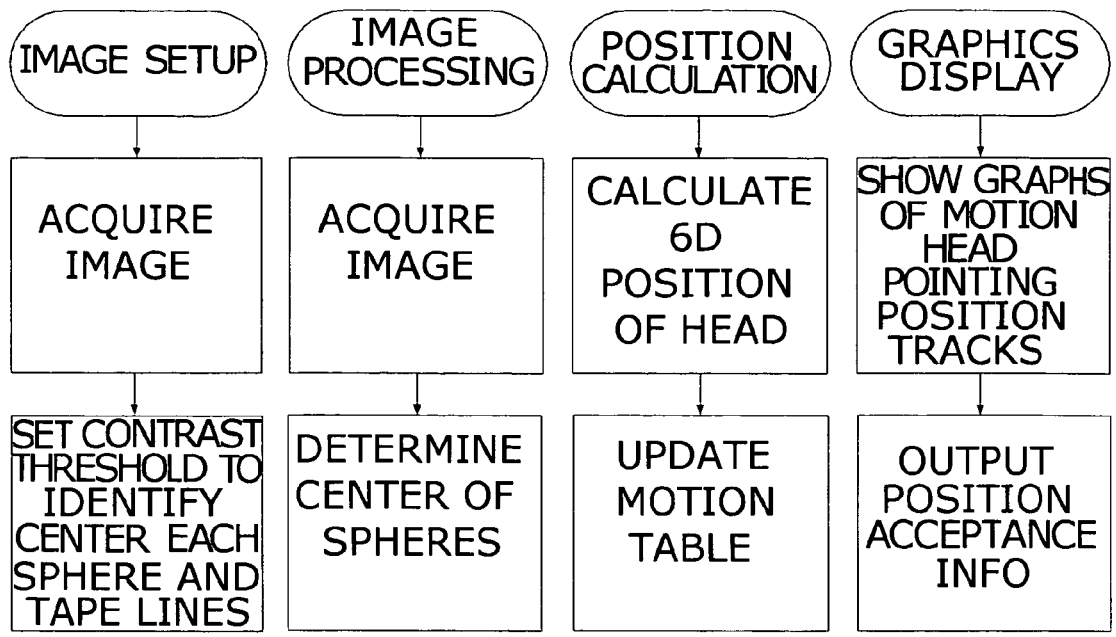
FIG. 8 is a block diagram, or flow chart, of movement processing according to the present invention.

FIG. 8 provides a diagram of the program steps of image processing. The program basically locates the 6 images of the 3 IR spheres to provide the X,Y, Z of each point and then inverts the matrix and uses a least squares operation to solve for the 3 points then solves for the 6D location of the top point of the head of the patient.

Figure 9:
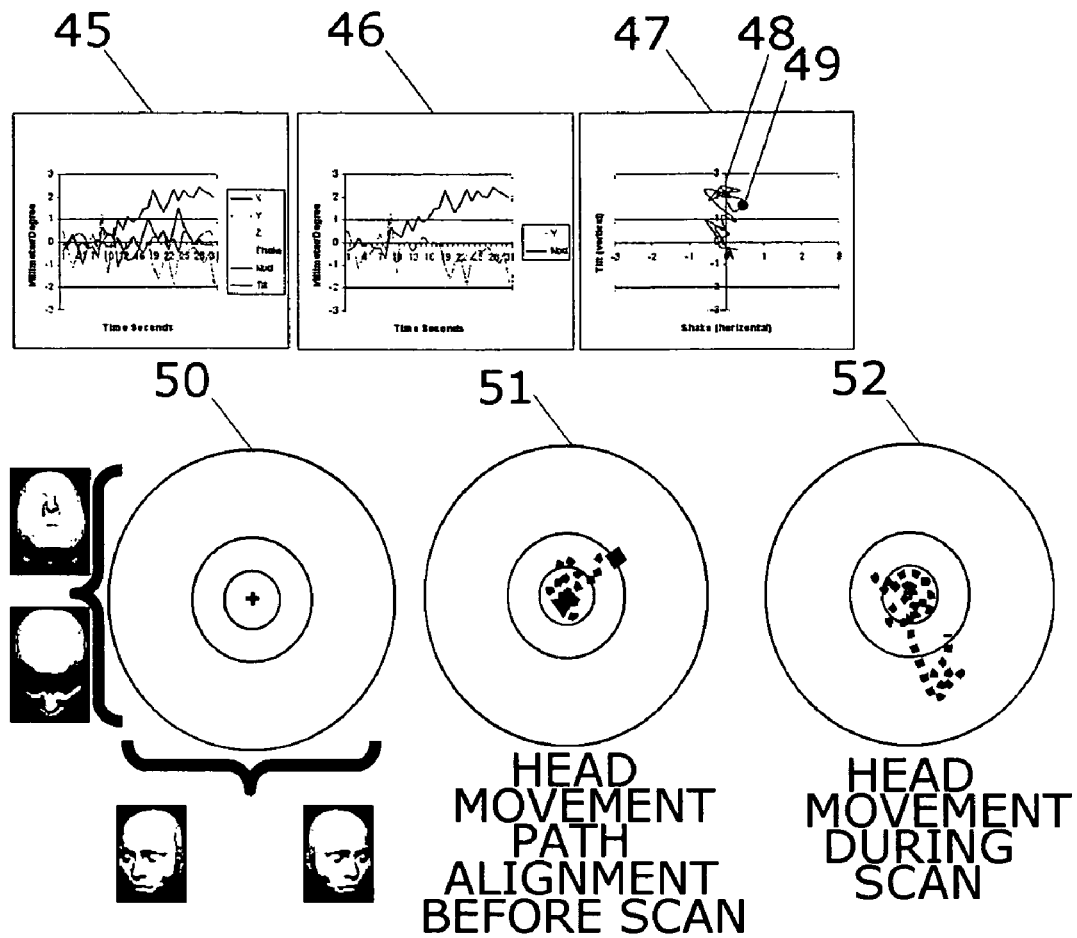
FIG. 9 is a series of potential visual displays of patient movement.
Figure 10:
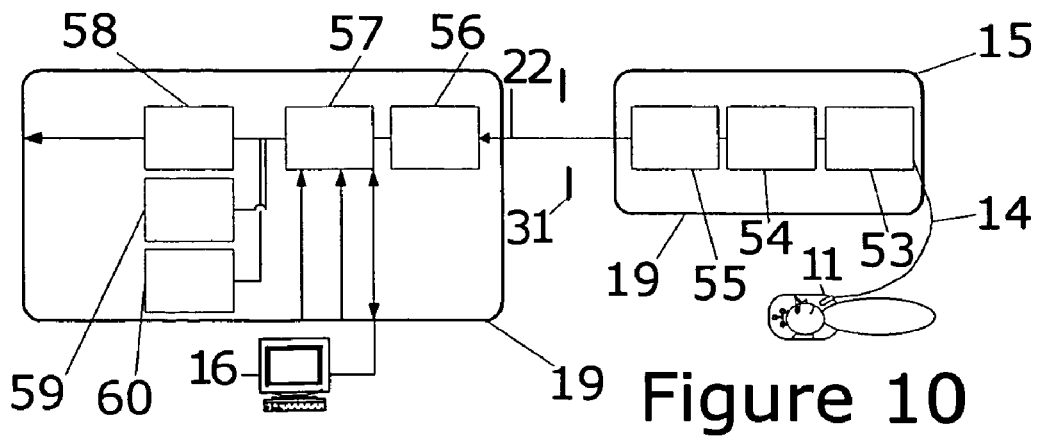
FIG. 10 is a schematic block diagram of the MRI microphone system according to the present invention.

FIG. 9 shows a variety of motion displays as might occur in a brain scanning run. Graph 45 of FIG. 9 shows the traditional 6D display providing X, Y, Z in millimeter displacement and head shaking (rotation on vertical axis), nodding (rotation on horizontal axis) and tilting (along depth axis of head). In this example the patient began moving at 10 seconds into the run and continued moving for 10 seconds. These 6D figures are difficult for technologists and patients to interpret because of the many dimensions. Graph 46 of FIG. 9 shows the data limited to only showing the dimensions that show unacceptable movement. Graph 47 of FIG. 9 shows a 2D figure of the principle problem directions in most scans of nodding and shaking. In this view as the patient or technologist sees the path 48 as a line and their current position as the bead 49 on that line (like the child toys of moving beads on wire shapes).

In a 2D target display 48 patients rapidly learn how to move their head to put the bead indicator on any location of the 2D surface. Sometimes in training children and adults they are given a cap with a laser pointer attached to the brim of the cap and are told to place the dot on the center of the target in the center of the bull's eye. As the patients move their head, they see a point moving on the display (similar to following a moving mouse on a computer display). The technologist demonstrates that wiggling a foot or moving a hand can result in a move of the head. Thus the patients learn how to remain still to enable accurate scanning.

In the MRI magnet multiple visual representations of the movement can be presented similar to those shown in FIG. 9. Display 50 of FIG. 9 shows the typical target display. The movement scales are shown with iconic heads to non-verbally communicate to the patient the directions of movement. At the beginning of a scanning run the patient would see Display 50. A moving dot would appear. Their task would be to move the dot to the center of the bull's eye as in Display 51 of FIG. 9. When they stay in the center green zone for 5 seconds the scanning begins. In structural scans the dot would continue to move and the patient would seek to keep the dot on the "+". In functional scans where patients must do a mental task, the movement display can be hidden to the patient while they are doing the task, so as not to be distracted. A method that is effective in children is to show the movement overlaid on a video of a cartoon. When the dot is in the green zone the video plays, when they venture out the video freezes till they return to the green zone. Children do not like to have their video paused and quickly learn to control their movements.

At the end of the scanning run, the movement display can reappear and be shown as a time compressed movement sequence (e.g., show 3 minutes of movement in fast speed mode in 10 seconds and stop playback at any points in time that movement was a problem and point that out to the patient). If the movement is too severe to support continued imaging, the scan run can be terminated, and restarted.

The system can use other modalities of feedback to control movement. For example auditory feedback and use high/low tones to indicate nodding of the head and volume differentiation of left and right ear to indicated head rotation. These can also have target zones (e.g., no sound if in the center of the bull's eye). Such feedback could be used with or without the projection display active.

There are many possible types of tracking of the movement and displays of the movement data. The innovations that make this system effective include a) rapid and accurate recording of position to provide immediate feedback to the patient/technician and the scanner, b) augmented displays that hide confusing information to the patient/technician enabling them to perceive the relationship of movement and head position, c) providing auditory movement cues if visual displays are not available (e.g., speech output saying "nod slightly down"), d) an instructional and training system that can develop movement control skills in the patient, e) a method to provide feedback so the patient can return the body part to the desired location, f) methods of identifying acceptable range of movement position, and g) methods to remove/present/replay the movement path to control when the patient attends to the movement image.

The MRI Forward Predictive Noise Canceling Microphone System is shown in FIG. 1 and FIG. 10-12. The preferred embodiment involves a microphone 11 that works in the MR magnet 3 (either wire or laser fiber optic), that is connected by wire or optic cable 14 to the MR Microphone amplifier/converter 15 typically in the magnet room 1 (though with the laser microphone the optic cable might pass through to the control room 2 directly). The in MR room amplifier 15 is in a Faraday cage to block high frequency RF. A filter blocks high frequency (over 20 KHz) RF from leaving the Faraday cage. A pre-amp 54 amplifies the signal, a Fiber optic converter converts the analog signal to digital and transmits on optical fiber. The optical fiber 22 conveys the signal to the control room 2. The optical converter converts the optical data to digital representation of the analog input. A Microprocessor performs the program schematically illustrated in FIG. 11 thereby recording and canceling the noise. The system outputs the data through a D/A converter and amplifiers to provide input to speakers for the technologist and to line output for audio recording and computer coding of the data. The system may have a buffer that can maintain multiple buffers of the audio input templates. A read-out may indicate to the technologist state information as to the nature of cancellation (indicating Pass Through, Acquisition, or Canceling). Control switches would allow the operator to set the system (e.g., auto mode, cancel mode, pass-through mode). There would be input from the MR machine indicating when scan volumes are recorded (e.g., on each TR of the acquisition). A USB control would allow optional input from the scanner or task computer 16 to set up the cancellation mode.

Figure 11:
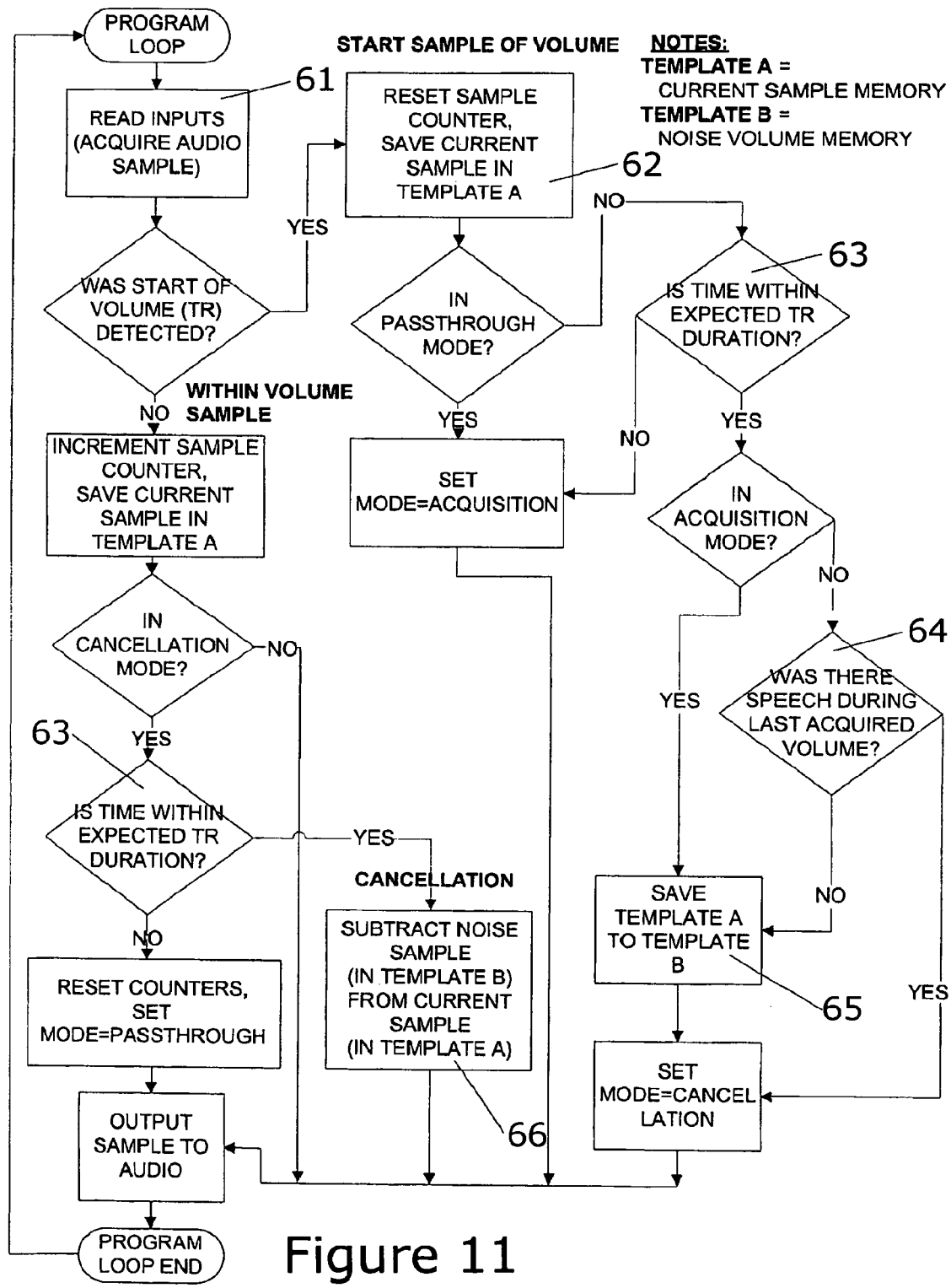
FIG. 11 is a schematic block diagram of MRI microphone sound processing used in the MRI microphone system according to the present invention.

FIG. 11 shows the program in the microprocessor performing the noise cancellation operations. The microprocessor would execute a short program loop typically at 44 KHz. On each cycle the microprocessor reads the input 61 reading the microphone input, input from the scanner signals, and input from operator switches. When the microprocessor senses the leading edge of the MR TR signal (or similar signal) the programs goes into the Yes Start Sample of Volume Phase 62. The program has three phases that determine action. The program is initiated in Pass-Through mode. In Pass-Through mode, the microprocessor simply reads the input and outputs it with a small (e.g., 10 micro-second) delay and looking for the leading edge of a TR event. When the first TR signal is sensed, the program state is set to Acquisition Mode to record the samples while passing the unmodified sound to the output. On the second TR, the program checks the duration 63 of the TR to see if it is within the time window (e.g., +/−20 microseconds) of the duration of the last TR. Note if the scan duration is not predictable, cancellation can not be performed. Normally noise cancellation with the present invention will begin after the third TR period. The first is used determine the duration, the second to verify the duration and record the sound template. Other implementations can feed the microprocessor the expected duration and the template such that cancellation could occur immediately with the first scan.

A key innovation of this approach is to use informed recent template approach and this is illustrated at flow chart item 64. The informed template involves using information to determine if the most recent recorded template is a clean noise template for the previous image or a contaminated template volume (e.g., speech+noise). It is considered a clean noise volume if the error from the previous volume (e.g., sum of squares of Acquired Sample−Template Sample for that time point) is below a preset threshold (this would likely detect if a person might be speaking). Additionally the technologist, task computer, or subject input could predict that speech was expected (e.g., in fMRI studies there are typically time windows were the patient is instructed to speak). If at anytime during a TR the input signals indicated expected speaking a dirty bit would be set, and that TR period would not be used as a template. If a pure noise volume occurred, the most recent template will be loaded as the template to be used for subtraction 65, if not the previous template would be used. During noise cancellation the most recent noise cancellation is used to subtract the magnet noise 66.

Figure 12:
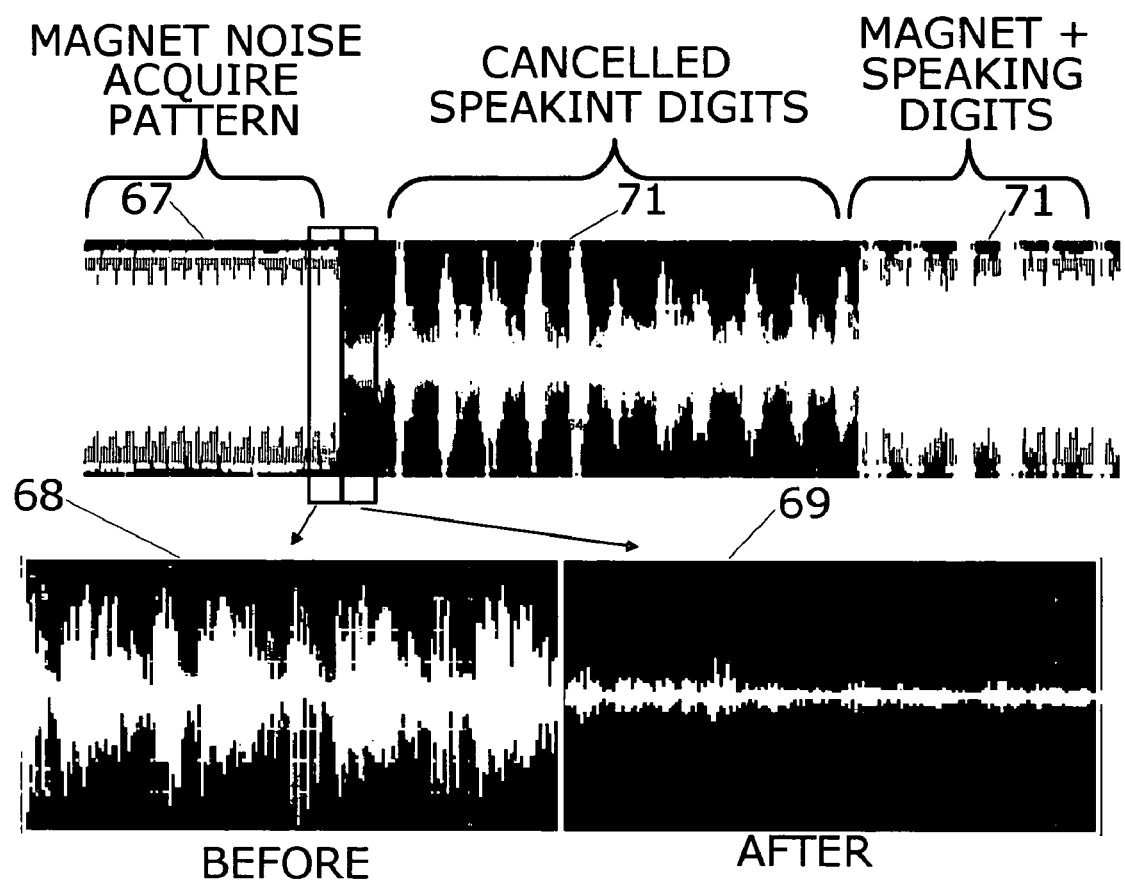
FIG. 12 is a diagram of auditory signal before and after noise cancellation.

The algorithm in FIG. 11 produces excellent noise cancellation. FIG. 12 illustrates the effect showing the acoustic wave forms recorded Dec. 06, 2003. The Left of waveform 67 illustrates the sound of the magnet background noise during pass through. Waveform 68 shows the noise waveform expanded. Waveform 69 shows the dramatic reduction in noise when the cancellation begins. Waveform 70 shows the waveform with cancellation with a person speaking digits. Note the clear envelope of the speech. Acoustically this sounds like clear speech with a mild hum in the background of the magnet noise. Step 71 shows what the sound looks like when the cancellation is turned off with the speech. It is hard to comprehend the words spoken and the envelope of voice onsets can not be discerned. Note some speech production procedures utilize the start of the voice onset time as a dependent measure. This is easily done during the cancellation 70, but not reliable during in the presence of the noise 71. This cancellation provides the patient with a safety mechanism allowing even soft communications to be discerned as might occur by an anxious patient.

The system also has a method of sensing patient speech. The microprocessor can trigger a signal (e.g., flashing light) to alert an occupied technician the patient is speaking (based on sensing that the incoming volume is not just scanner sound (see 64 FIG. 11). This for example can detect 70 db speech during the MRI scanning that includes 120 db scanner noise.

In some implementations the system will have multiple buffers allowing the past speech to be replayed by the technologist.

Above is described the preferred implementation of the present invention but is not intended to be restrictive thereof. Other variants would be used depending on the availability of signals from the scanner and the nature of the MRI pulse sequence. For example the acoustic wave form can be directly assessed for the repeating sound and used to determine the repeat interval in the absence of the scanner TR signal (this however has more estimate variability than the microsecond pulse from the scanner when it is available). Some scanner pulse sequences have very rhythmic noise (e.g., the acquire patterns uniformly over TR) and some acquire the images in burst mode (e.g., acquire multiple images at the beginning of the TR and then have a period of silence). The cancellation algorithm above will work for this if the TR trigger signal is provided. If the scanner provides other signals (e.g., for each gradient pulse) the program might have to be informed how many such pulses produce a TR and then cancellation can proceed.

The combination of forward cancellation, information about the likelihood of speaking, and use of recent template cancellation enables the system to continuously update the template whenever the patient is not speaking and adapt to small changes in the acoustic environment that might occur as the patient makes small movements (e.g., moves their hand). The checking of variation in the TR timing allows the system to operate in automatic mode starting cancellation on the second TR and turning off cancellation when the scan recording stops typically with no input from the operator.

The three MRI systems discussed above solve critical needs for MRI patient instruction/testing/comfort, motion control, and speech communication. The MRI Digital Video Projection System provides better quality display to the patient to better inform, instruct, test, and comfort the patient plus the potential to stimulate the brain with microsecond onset times to better diagnose brain function. The MRI Motion Tracker and Patient Augmented Feedback System enables monitoring patient head (or body part) motion and providing real time feedback to the patient that can substantially improve diagnostic yield of scanning sessions particularly for children and mentally challenged individuals. The MR Forward Predictive Noise Canceling Microphone System removes the intense MRI acoustic noise improving patient communication, patient safety and enabling coding of speech output. These systems can be used individually but maximum benefit is from providing all three. For example having the patient speak is useful in mapping language areas of the brain in surgical planning (i.e., the surgeon does not want to remove speech production making the patient mute). To map brain function for speaking, the noise cancellation microphone enables accurate coding of the spoken words and tracking the onset times of utterances. However, when people speak they tend to move their head degrading the imaging quality. The motion tracker provides a method to track the motion and train the patient to minimize that motion. The motion tracker uses the display of the digital video to easily convey the information to the patient. The end result is better imaging that leads to more effective medical care. Various modifications may be made to the systems of the present invention without departing from the scope and content of the present invention. The present invention is intended to encompass such modifications, the scope and content of the present invention being defined by the appended claims and equivalents thereto.

What is claimed is:

1. An MRI system comprising:

A magnet room;

A magnet within the magnet room defining a patient receiving magnet bore;

A control room associated with the magnet room; and an MRI forward predictive noise cancellation microphone system including:

a. a microphone within the magnet room, the microphone adapted to receive both acoustic noise alone within the magnet room that forms a cancellation template and a combination of acoustic noise and patient speech within the magnet room, b. at least one receiving device outside the magnet room; and c. a controller receiving signals from the microphone and outputting an audio signal to the at least one receiver, (i) wherein the controller can operate in cancellation mode which subtracts the cancellation template from the signal received from the microphone, (ii) wherein the controller updates the cancellation template with a previous received signal that has been determined to be acoustic noise alone, and (iii) wherein the controller receives input from at least one of the technician, the patient and an MRI system controller that is indicative of patient speech occurring whereby the signal from the microphone will be considered acoustic noise and patient speech and will not be used to update the cancellation template, and wherein the system includes At least one of A) an MRI digital projection system for the MRI system including a. a source of video signal outside the magnet room, the source including a digital video interface;

b. a digital video interface/fiber optic converter coupled to the video signal source;

c. a fiber optic cable coupled to the digital video interface/fiber optic converter extending from the digital video interface/fiber optic converter into the magnet room;

d. a fiber optic/digital interface converter within the magnet room and coupled to a distal end of the fiber optic cable;

e. a digital light processing projector within the magnet room and coupled to the fiber optic/digital interface converter;

f. a screen positioned within the magnet room and viewable by the patient within the magnet bore and configured to receive a viewable image from the digital light processing projector; and g. RF shielding within the magnet room extending around at least the fiber optic/digital interface converter and the digital light projector; or B) an MRI digital projection system for the MRI system including:

a. a source of video signal outside the magnet room, the source including a digital video interface;

b. a digital video interface/fiber optic converter coupled to the video signal source;

c. a fiber optic cable coupled to the digital video interface/fiber optic converter extending from the digital video interface/fiber;

d. a fiber optic/digital interface converter coupled to a distal end of the fiber optic cable;

e. a digital light processing projector coupled to the fiber optic/digital interface converter, the projector including a RGB color wheel that spins at a determined frequency;

f. a screen positioned within the magnet room and viewable by the patient within the magnet bore and configured to receive a viewable image from the digital light processing projector; and g. a synchronization unit for synchronizing the images on the screen, wherein the synchronization unit utilizes a control signal from the determined frequency of the color wheel; and wherein the Digital Light Processing Projector of the digital projection system of A) or B) utilizes a wave guide attached thereto to project the image onto the screen through one of a prism or mirror.

2. The MRI system of claim 1 wherein the system includes an MRI body part motion tracking system including: a. a visible target attached a body part of the patient within the magnet room; b. a camera for viewing the target; c. a body part position determination unit for receiving sequential images from the camera of the target on the body part of the patient, in which the relative position of the body part of the patient associated with the target is calculated based upon the images of the target; and d. A feedback mechanism for providing a real time feedback of the calculated relative body position to at least one of the technician and the patient, wherein the real time feedback is at least one of a visual and auditory signal.

3. The MRI system of claim 2 wherein the target is attached to the patients head and includes a plurality of spaced infrared reflectors.

4. The MRI system of claim 3 wherein the MRI digital projection system for the MRI system is the system of part A) and the camera is positioned within the RF cage.

5. The MRI system of claim 3 wherein the real time display of the calculated relative body position is provided to the patient through the MRI digital projection system.

6. The MRI system of claim 5 wherein the real time display of the calculated relative body position is provided to the technician.

7. The MRI system of claim 1 wherein the controller of the MRI forward predictive noise cancellation system compares the signal of a noise only segment to the existing noise cancellation template and replaces the existing noise cancellation template with the new noise only segment only if the difference between the two signals is below a set threshold.

8. The MRI system of claim 7 wherein the system includes an MRI body part motion tracking system including: a. a visible target attached a body part of the patient within the magnet room; b. a camera for viewing the target; c. a body part position determination unit for receiving sequential images from the camera of the target on the body part of the patient, in which the relative position of the body part of the patient associated with the target is calculated based upon the images of the target; and d. A feedback mechanism for providing a real time feedback of the calculated relative body position to at least one of the technician and the patient, wherein the real time feedback is at least one of a visual and auditory signal.

9. The MRI system of claim 8 wherein the target is attached to the patients head and includes a plurality of spaced infrared reflectors.

10. An MRI forward predictive noise cancellation microphone system comprising:
A) a microphone configured for use within an MRI magnet room, the microphone receiving both acoustic noise alone within the magnet room that forms a cancellation template and a combination of acoustic noise and patient speech within the magnet room,
B) at least one receiving device outside the magnet room; and
C) a controller receiving signals from the microphone and outputting an audio signal to the at least one device,
(i) wherein the controller can operate in cancellation mode which subtracts the cancellation template from the signal received from the microphone,
(ii) wherein the controller updates the cancellation template with the last received signal that has been determined to be acoustic noise alone, and
(iii) wherein the controller receives input from at least one of the technician, the patient and an MRI system controller that is indicative of patient speech occurring whereby the signal from the microphone will be considered acoustic noise and patient speech and will not be used to update the cancellation template, wherein the controller of the MRI forward predictive noise cancellation system compares the signal of a noise only segment to the existing noise cancellation template and replaces the existing noise cancellation template with the new noise only segment only if the difference between the two signals is below a set threshold.

11. An MRI digital projection system for the MRI system including
A) a source of video signal outside an MRI magnet room, the source including a digital video interface;
B) a digital video interface/fiber optic converter coupled to the video signal source;
C) a fiber optic cable coupled to the digital video interface/fiber optic converter extending from the digital video interface/fiber optic converter into the magnet room;
D) a fiber optic/digital interface converter within the magnet room and coupled to a distal end of the fiber optic cable;
E) a digital light processing projector within the magnet room and coupled to the fiber optic/digital interface converter;
F) a screen positioned within the magnet room and viewable by the patient within the magnet bore and configured to receive a viewable image from the digital light processing projector; and
G) RF shielding within the magnet room extending around at least the fiber optic/digital interface converter and the digital light processing projector.

12. An MRI digital projection system for the MRI system comprising:
A) a source of video signal outside and MRI magnet room, the source including a digital video interface;
B) a digital video interface/fiber optic converter coupled to the video signal source;
C) a fiber optic cable coupled to the digital video interface/fiber optic converter extending from the digital video interface/fiber;
D) a fiber optic/digital interface converter coupled to a distal end of the fiber optic cable;
E) a digital light processing projector coupled to the fiber optic/digital interface converter, the projector including a RGB color wheel that spins at a determinable frequency;
F) a screen positioned within the magnet room and viewable by the patient within the magnet bore and configured to receive a viewable image from the digital light projector; and
G) a synchronization unit for synchronizing the images on the screen, wherein the synchronization unit utilizes a control signal from the determined frequency of the color wheel.

13. The MRI digital projection system for the MRI system according to claim 12 further including a MRI forward predictive noise cancellation microphone system comprising:

A) a microphone configured for use within an MRI magnet room, the microphone receiving both acoustic noise alone within the magnet room that forms a cancellation template and a combination of acoustic noise and patient speech within the magnet room,
B) at least one receiving device outside the magnet room; and
C) a controller receiving signals from the microphone and outputting an audio signal to the at least one device,
  (i) wherein the controller can operate in cancellation mode which subtracts the cancellation template from the signal received from the microphone,
  (ii) wherein the controller updates the cancellation template with the last received signal that has been determined to be acoustic noise alone, and
  (iii) wherein the controller receives input from at least one of the technician, the patient and an MRI system controller that is indicative of patient speech occurring whereby the signal from the microphone will be considered acoustic noise and patient speech and will not be used to update the cancellation template.

14. The MRI digital projection system for the MRI system according to claim 11 further including a MRI forward predictive noise cancellation microphone system comprising:

A) a microphone configured for use within an MRI magnet room, the microphone receiving both acoustic noise alone within the magnet room that forms a cancellation template and a combination of acoustic noise and patient speech within the magnet room,
B) at least one receiving device outside the magnet room; and
C) a controller receiving signals from the microphone and outputting an audio signal to the at least one device,
  (i) wherein the controller can operate in cancellation mode which subtracts the cancellation template from the signal received from the microphone,
  (ii) wherein the controller updates the cancellation template with the last received signal that has been determined to be acoustic noise alone, and
  (iii) wherein the controller receives input from at least one of the technician, the patient and an MRI system controller that is indicative of patient speech occurring whereby the signal from the microphone will be considered acoustic noise and patient speech and will not be used to update the cancellation template.

* * * * *